United States Patent [19]

Hlatky et al.

[11] Patent Number: 5,241,025
[45] Date of Patent: Aug. 31, 1993

[54] CATALYST SYSTEM OF ENHANCED PRODUCTIVITY

[75] Inventors: Gregory G. Hlatky, Houston; Howard W. Turner, Webster, both of Tex.

[73] Assignee: Exxon Chemical Patents Inc., Linden, N.J.

[21] Appl. No.: 955,764

[22] Filed: Oct. 2, 1992

Related U.S. Application Data

[63] Continuation of Ser. No. 496,378, Mar. 20, 1990, Pat. No. 5,153,157, which is a continuation-in-part of Ser. No. 133,480, Dec. 22, 1987, abandoned, which is a continuation-in-part of Ser. No. 8,800, Jan. 30, 1987, abandoned.

[51] Int. Cl.$^5$ ............................................. C08F 4/642
[52] U.S. Cl. ..................... 526/129; 526/132; 526/133; 526/134; 526/156; 526/160; 502/103; 502/108; 502/117
[58] Field of Search ............... 526/129, 132, 133, 134, 526/160, 156

[56] References Cited

U.S. PATENT DOCUMENTS

| | | | |
|---|---|---|---|
| 5,064,802 | 11/1991 | Stevens et al. | 526/134 X |
| 5,066,741 | 11/1991 | Campbell | 526/160 X |

FOREIGN PATENT DOCUMENTS

| | | |
|---|---|---|
| 277003 | 8/1988 | European Pat. Off. . |
| 277004 | 8/1988 | European Pat. Off. . |
| 426637 | 5/1991 | European Pat. Off. . |
| 426638 | 5/1991 | European Pat. Off. . |
| 427696 | 5/1991 | European Pat. Off. . |
| 427697 | 5/1991 | European Pat. Off. . |

*Primary Examiner*—Patrick P. Garvin
*Attorney, Agent, or Firm*—M. Susan Spiering; Myron B. Kurtzman

[57] ABSTRACT

This invention relates to catalyst systems, and a method for using such system, for the enhanced production of homo and copolymer products of olefin, diolefin and/or acetylenically unsaturated monomers. This invention catalyst system comprises a Group III-A element compound for improving the productivity of an olefin polymerization catalyst which is the reaction product of a metallocene of a Group IV-B transition metal and an ionic activator compound comprising a cation capable of donating a proton which will irreversibly react with at least one ligand contained in the Group IV-B metal compound and an anion which is bulky, labile and non-coordinateable with the Group IV transition metal cation produced upon reaction of the metallocene and activator compound to form the catalyst component of the catalyst system.

15 Claims, No Drawings

CATALYST SYSTEM OF ENHANCED PRODUCTIVITY

CROSS REFERENCE TO RELATED APPLICATIONS

This application is a continuation of copending U.S. application Ser. No. 496,378 filed Mar. 20, 1990 and now U.S. Pat. No. 5,153,157, which is a continuation-in-part of copending U.S. patent application Ser. No. 133,480 filed Dec. 22, 1987 and now abandoned. U.S. Ser. No. 133,480 is in turn a continuation-in-part of U.S. Ser. No. 008,800 filed Jan. 30, 1987 and now abandoned.

Background of the Invention

1. Field of the Invention

This invention relates to the use of organometallic compounds for improving the productivity of ionic metallocene olefin polymerization catalysts. These catalysts are the reaction product of metallocenes of a Group IV-B transition metal and ionic activator compounds. These ionic metallocene catalyst systems have enhanced productivity over similar catalysts not using the organometallic compounds. These catalysts are useful for the polymerization of olefins, diolefins, cyclic olefins and acetylenically unsaturated monomers to polyolefins having narrow molecular weight distributions and higher weight average molecular weights than heretofore attainable with a like metallocene which is activated to an active catalyst species of reaction with an aluminum alkyl or alumoxane cocatalyst.

2. Background

Ziegler-Natta type catalyst for the polymerization of olefins are well known. The traditional Ziegler-Natta type soluble systems comprise a metal halide activated to a catalyst species by reaction with a metal alkyl cocatalyst, particularly an aluminum alkyl cocatalyst. The activation of these traditional heterogeneous Ziegler-Natta catalysts generates a variety of different active sites. As a consequence of this non-uniformity of the active sites, the catalysts produce polymer products having a broad molecular weight distribution (MWD). Furthermore, the polymer product exhibit broad composition distribution (CD), poor comonomer incorporation and block sequence distribution.

Recently it has been found that active catalysts are formed with a bis(cyclopentadienyl) compound of the Group IV-B metals, including zirconium and hafnium, is activated by an alumoxane. The metallocene-alumoxane catalysts, whether homogeneous or supported, generally possess high activity and are more versatile than conventional Ziegler-Natta type catalysts in that they may be effectively used to produce a variety of polymer products including, for example, high density linear polyethylene (HDPE), linear low density polyethylene (LLDPE), ethylene-propylene copolymer (EP), non-crystalline polypropylene and crystalline polypropylene. The metallocene-alumoxane catalysts also offer the significant advantage over the traditional Ziegler-Natta catalysts of being able to produce polymers with narrow MWD.

While the metallocene-alumoxane catalysts do offer significant advantages over the traditional Ziegler-Natta catalysts, they nevertheless have limitations in practical commercial applications. These limitations include the relatively high cost of the alumoxane cocatalysts. Alumoxane is also air sensitive and difficult to manipulate. Furthermore, the metallocene-alumoxane catalyst, while producing a narrow MWD polymer product, have a limited capability to produce high molecular weight polymers or polymers having a high comonomer content.

European Patent Application 277,003 and 277,004 (1988), which are hereby incorporated by reference, describe a further advance in metallocene catalysts: new metallocene catalysts which do not require either an alkyl aluminum or an alumoxane as an activator. The Group IV-B metallocene catalysts are prepared as a reaction product of a Group IV-B metal metallocene compound and an ionic activator compound. The ionic activator comprises a cation having a donatable proton or which will irreversibly react with at least one ligand contained in the Group IV-B metal compound and a labile, bulky anion. The bulk of said anion is such that upon reaction of the donatable proton with a substituent of a bid(cyclopentadienyl) Group IV-B metal compound, which reacts with proton forming a group IV-B metal cation, the anion of the activator is sterically hindered from covalently coordinating to the Group IV-B metal cation. Hence, as described in our copending applications, an active catalytic species of a metallocene is formed, namely an ionic pair comprising a metallocene transition metal cation paired with a noncoordinating anion of the activator component.

The new metallocene catalyst systems (hereafter referred to as an "ionic metallocene catalysts") eliminate the need for an expensive alumoxane activator. The ionic metallocene catalyst also offer other advantages over the metallocene-alumoxane catalysts such as permitting the production of polyolefine products of narrow MWD and of significantly higher weight average molecular weight at high rates of catalytic activity while also permitting better incorporation of comonomers and the control of the chain end chemistry of the polymer products.

It is believed that the active catalytic species in the metallocene alumoxane catalysts is an ion pair. It is also believed that this ion pair active species is formed through a Lewis acid-Lewis base reaction of two neutral components (the metallocene and the alumoxane) leading to an equilibrium between a neutral, apparently catalytically inactive adduct, and an ion pair complex which is presumably the active catalyst. As a result of this equilibrium, there is a competition for the anion which must be present to stabilize the active Group IV-B metal cation of the active catalyst species. In the case of the ionic metallocene catalyst described herein, the metallocene and the activator react irreversibly and the equilibrium almost exclusively favors the catalytically active ion pair complex. Hence, the new ionic metallocene catalyst has a very high activity and is able to produce polyolefin products of high molecular weight and narrow molecular weight distribution.

It has been discovered that the activity of the active catalytic ion pair species of our ionic catalyst can be unexpectedly and significantly improved by removing impurities contained in the polymerization diluent or the monomer supply, catalyst is used. The most prominent impurities present in a polymerization diluent and/or a monomer are oxygen and water. Despite the most elaborate control, some, although minute, quantity of such impurities will invariably be present in a polymerization diluent and/or the monomer supply.

SUMMARY OF THE INVENTION

The invention provides a catalyst system comprising an ionic metallocene catalyst and an additive which removes impurities which may deactivate the ionic metallocene catalysts. The catalyst system, like the ionic metallocene catalyst without additives disclosed in European Patent Applications 277,003 and 277,004 (1988) permits the production of polyolefins of high molecular weight and narrow molecular weight distribution (MWD). Moreover, the polyolefin products of the catalyst system have a narrow comonomer distribution (CD) approaching randomness and improved sequence distribution of comonomers as compared to the products of prior art metallocene-alumoxane supported catalysts. Further, like the ionic metallocene catalysts of the copending applications, the catalyst systems are useful in the polymerization of olefins, diolefins, and/or acetylenically unsaturated monomers either alone or in combination with each other. However, the addition of an additive which neutralizes those impurities capable of deactivating the active catalytic sites of the ionic metallocene catalyst provides a catalyst system of greatly improved productivity without significantly affecting molecular weight or extent of comonomer incorporation.

The additive component of the catalyst system can be any material which will neutralize the undesirable impurities without adversely affecting the catalyst.

IONIC CATALYST SYSTEM—GENERAL DESCRIPTION

The process of this invention is practiced with that class of ionic catalysts referred to, disclosed, and described in European Patent Applications 277,003 and 277,004. The ionic catalyst is prepared by combining at least two components. The first of these is a bis(cyclopentadienyl) derivative of a Group IV-B metal compound containing at least one ligand which will combine with the second component or at least a portion thereof such as a cation portion thereof. The second component is an ion-exchange compound comprising a cation which will irreversibly react with at least one ligand contained in said Group IV-B metal compound and a noncoordinating anion which is bulky, labile, and stable. Upon combination of the first and second components, the cation of the second component reacts with one of the ligands of the first component, thereby generating an ion pair consisting of a Group IV-B metal cation with a formal coordination number of 3 and a valence of +4 and the aforementioned anion, which anion is compatible with and non-coordinating towards the metal cation formed from the first component. The anion of the second compound must be capable of stabilizing the Group IV-B metal cation complex without interfering with the Group IV-B metal cation's or its composition product's ability to function as a catalyst and must be sufficiently labile to permit displacement by an olefin, diolefin or an acetylenically unsaturated monomer during polymerization.

A. The Metallocene Component

The Group IV-B metal compounds, useful as first compounds in the ionic catalyst system employed in the process of this invention are the bis(cyclopentadienyl) derivatives of titanium, zirconium and hafnium compounds may be represented by the following general formulae:

$$(A-Cp)MX_2X_x \quad (1)$$

$$-(A-Cp)MX_1X_2 \quad (2)$$

$$(A-Cp)Ml \quad (3)$$

$$-(Cp)(RCp)MX_1$$

wherein: M is a metal selected from the Group consisting of titanium (Ti), zirconium (Zr) and hafnium (Hf); (A—Cp) is either (Cp)(Cp*) or Cp—A'—Cp* and Cp and Cp* are the same or different substituted or unsubstituted cyclopentadienyl radicals, R is a substituent covalently bonded to the the cyclopentadiene ring and wherein A' is a covalent bridging group; L is an olefin, diolefin or aryne ligand; $X_1$ and $X_2$ are, independently, selected from the Group consisting of hydride radicals, hydrocarbyl radicals having from 1 to 20 carbon atoms, substituted-hydrocarbyl radicals, wherein one or more of the hydrogen atoms are replaced with a halogen atom, having from 1 to about 20 carbon atoms, organo-metalloid radicals comprising a Group IV-A element wherein each of the hydrocarbyl substituents contained in the organo-portion of said organo-metalloid, independently, contain from 1 to about 20 carbon atoms and the like; $X'_1$ and $X'_2$ are joined and bound to the metal atoms to form a metallacycle, in which the metal, $X'_1$ and $X'_2$ form a hydrocarbocyclic ring containing from about 3 to about 20 carbon atoms; and R is a substituent, preferably a hydrocarbyl substituent, having from 1 to 20 carbon atoms, on one of the cyclopentadienyl radicals which is also bound to the metal atom.

Each carbon atom in the cyclopentadienyl radical may be, independently, unsubstituted (H) or substituted with the same or a different radical selected from the Group consisting of hydrocarbyl radicals, substituted-hydrocarbyl radicals wherein one or more hydrogen atoms is replaced by a halogen atom, hydrocarbyl-substituted metalloid radicals wherein the metalloid is selected from Group IV-A of the Periodic Table of the Elements, halogen radicals and the like. Suitable hydrocarbyl and substituted-hydrocarbyl radicals which may be substituted for at least one hydrogen atom in the cyclopentadienyl radical will contain from 1to about 20 carbon atoms and include straight and branched alkyl radicals, cyclic hydrocarbon radicals, alkyl-substituted aromatic radicals. Similarly, and when $X_1$ and/or $X_2$ is a hydrocarbyl or substituted-hydrocarbyl radical, each may, independently, contain from 1 to about 20 carbon atoms and be a straight or branched alkyl radical, a cyclic hydrocarbyl radical, an alkyl-substituted cyclic hydrocarbyl radical, an aromatic radical or an alkyl-substituted aromatic radical. Suitable organo-metalloid radicals include mono-, or di- and trisubstituted organo-metalloid radicals of Group IV-A elements wherein each of the hydrocarbyl Groups contain from 1 to about 20 carbon atoms. Suitable organo-metalloid radicals include trimethylsilyl, tri-ethysilyl, ethyldimethylsilyl, methyldiethylsily, triphenylgermyl, trimethylgermyl and the like.

Illustrative, but not limiting examples of bis(cyclopentadienyl)zirconium compounds which may be used in the preparation of the improved catalyst of this invention are dihydrocarbyl-substituted bis(cyclopentadienyl)zirconium compounds such as bis(cyclopentadienyl)zirconium dimethyl, bis(cyclopentadienyl)zirconium diethyl, bis(cyclopentadienyl)zirconium dipropyl, bis(cyclopentadienyl)zirconium dibutyl, bis(cyclopentadienyl)zirconium diphenyl, bis(cyclopentadienyl)zirconium dineopentyl, bis(cyclopentadienyl)zirconium di(m-tolyl), bis(cyclopentadienyl)zirconium di(p-tolyl) and the like; (monohydrocarbyl-substituted cyclopentadienyl)zirconium compounds such as (methylcyclopentadienyl)cyclopentadienyl) and bis(methylcyclopentadienyl)zirconium dimethyl, (ethylcyclopentadienyl) (cyclopentadienyl) and bis(ethylcyclopentadienyl)zirconium dimethyl, (propylcyclopentadienyl)(cyclopentadienyl) and bis(propylcyclopentadienyl)zirconium dimethyl, (n-butylcyclopentadienyl)(cyclopentadienyl) and bis(n-butylcyclopentadienyl)zirconium dimethyl, (t-butylcyclopentadienyl) (cyclopentadienyl) and bis(t-butylcyclopentadienyl)zirconium dimethyl, (cyclohexylmethylcyclopentadienyl) (cyclopentadienyl) and bis(cyclohexylmethylcyclopentadienyl)zirconium dimethyl, (benzylcyclopentadienyl) (cyclopentadienyl) and bis(benzylcyclopentadienyl)zirconium dimethyl, (diphenylmethylcyclopentadienyl) (cyclopentadienyl) and bis(diphenylmethylcyclopentadienyl)zirconium dimethyl, (methylcyclopentadienyl) (cyclopentadienyl) and bis(methylcyclopentadienyl)zirconium dihydride, (ethylcyclopentadienyl)(cyclopentadienyl) and bis(ethylcyclopentadienyl)zirconium dihydride, (propylcyclopentadienyl)(cyclopentadienyl) and bis(propylcyclopentadienyl)zirconium dihydride, (n-butylcyclopentadienyl)(cyclopentadienyl) and bis(n-butylcyclopentadienyl)zirconium dihydride, (t-butylcyclopentadienyl)(cyclopentadienyl) and bis(t-butylcyclopentadienyl)zirconium dihydride, (cyclohexylmethylcyclopentadienyl)(cyclopentadienyl) and bis(cyclohexylmethylcyclopentadienyl)zirconium dihydride, (benzylcyclopentadienyl)(cyclopentadienyl) and bis(benzylcyclopentadienyl)zirconium dihydride, (diphenylmethylcyclopentadienyl)(cyclopentadienyl) and bis(diphenylmethylcyclopentadienyl)zirconium dihydride and the like; (polyhydrocarbyl-substituted-cyclopentadienyl) zirconium compounds such as (dimethylcyclopentadienyl) (cyclopentadienyl) and bis(dimethylcyclopentadienyl)zirconium dimethyl, (trimethylcyclopentadienyl) (cyclopentadienyl) and bis(trimethylcyclopentadienyl)zirconium dimethyl, (tetramethylcyclopentadienyl) (cyclopentadienyl) and bis(tetramethylcyclopentadienyl)zirconium dimethyl, (permethylcyclopentadienyl) (cyclopentadienyl) and bis(permethylcyclopentadienyl)zirconium dimethyl, (ethyltetramethylcyclopentadienyl) (cyclopentadienyl) and bis(ethyltetramethylcyclopentadienyl)zirconium dimethyl, (indenyl)(cyclopentadienyl) and bis(idenyl)zirconium dimethyl, (dimethylcyclopentadienyl) and (cyclopentadienyl) and bis(dimethylcyclopentadienyl) zirconium dihydride, (trimethylcyclopentadienyl) (cyclopentadienyl) and bis(trimethylcyclopentadienyl) zirconium dihydride, (tetramethylcyclopentadienyl) (cyclopentadienyl) and bis(tetramethylcyclopentadienyl) zirconium dihydride, (permethylcyclopentadienyl) (cyclopentadienyl) and bis(permethylcyclopentadienyl) zirconium dihydride, (ethyltetramethylcyclopentadienyl) (cyclopentadienyl) and bis(ethyltetramethylcyclopentadienyl) zirconium dihydride, (indenyl)(cyclopentadienyl) and bis(indenyl)zirconium (propylcyclopentadienyl) (cyclopentadienyl) and (bis(proylcyclopentadienyl)zirconium dihydride, (n-butylcyclopentadienyl) (cyclopentadienyl) and bis(n-butylcyclopentadienyl)zirconium dihydride, (t-butylcyclopentadienyl) (cyclopentadienyl) and bis(t-butylcyclopentadienyl)zirconium dihydride, (cyclohexylmethylcyclopentadienyl) (cyclopentadienyl) and bis(cyclohexylmethylcyclopentadienyl)zirconium dihydride, (benzylcyclopentadienyl) (cyclopentadienyl) and bis(benzylcyclopentadienyl)zirconium dihydride, (diphenylmethylcyclopentadienyl) (cyclopentadienyl) and bis(diphenylmethylcyclopentadienyl)zirconium dihydride and the like; (polyhydrocarbyl-substituted-cyclopentadienyl) zirconium compounds such as (dimethylcyclopentadienyl) (cyclopentadienyl) and bis(dimethylcyclopentadienyl) and bis(dimethylcyclopentadienyl)zirconium dimethyl, (trimethylcyclopentadienyl) (cyclopentadienyl) and bis(trimethylcyclopentadienyl)zirconium dimethyl, (tetramethylcyclopentadienyl) (cyclopentadienyl) and bis(tetramethylcyclopentadienyl)zirconium dimethyl, (permethylcyclopentadienyl) (cyclopentadienyl) and bis(permethylcyclopentadienyl)zirconium dimethyl, (ethyltetramethylcyclopentadienyl) (cyclopentadienyl) and bis(ethyltetramethylcyclopentadienyl)zirconium dihydride, (indenyl)(cyclopentadienyl) and bis(indenyl)zirconium dihydride and the like; (metal hydrocarbyl-substituted cyclopentadienyl)zirconium compounds such as (trimethylsilylcyclopentadienyl)(cyclopentadienyl) and bis(trimethylsilylcyclopentadienyl)zirconium dimethyl, (trimethylgermylcyclopentadienyl)(cyclopentadienyl) and bis(trimethylgermylcyclopentadienyl)zirconium dimethyl, (trimethylstannylcyclopentadienyl)(cyclopentadienyl) and bis(trimethylstannylcyclopentadienyl)zirconium dimethyl, (trimethylplumbylcyclopentadienyl)(cyclopentadienyl) and bis(trimethylplumbylcyclopentadienyl)zirconium dimethyl, (trimethylsilylcyclopentadienyl)(cyclopentadienyl) and bis(trimethylsilylcyclopentadienyl)zirconium dihydride, (trimethylgermylcyclopentadienyl)(cyclopentadienyl) and bis(trimethylgermylcyclopentadienyl)zirconium dihydride, (trimethylstannylcyclopentadienyl)(cyclopentadienyl) and bis(trimethylstannylcyclopentadienyl)zirconium dihydride, (trimethylplumbylcyclopentadienyl)(cyclopentadienyl) and bis(trimethylplumbylcyclopentadienyl)zirconium dihydride and the like; (halogen-substituted-cyclopentadienyl) zirconium compounds such as (trifluoromethylcyclopentadienyl)-(cyclopentadienyl) and bis(trifluoromethylcyclopentadienyl)zirconium dimethyl (trifluoromethylcyclopentadienyl)(cyclopentadienyl) and bis(trifluoromethylcyclopentadienyl)zirconium dihydride and the like; silyl-substituted bis(cyclopentadienyl) zirconium compounds such as bis(cyclopentadienyl) (trimethylsilyl)(methyl)-zirconium, bis(cyclopentadienyl) (triphenylsilyl)(methyl)zirconium, bis(cyclopentadienyl) [tris((dimethylsilyl)silyl](methyl)zirconium, bis(cyclopentadienyl) [bis(mesityl)silyl](methyl)zirconium, bis(cyclopentadienyl)(trimethylsilyl)trimethylsilylmethyl) zirconium, bis(cyclopentadienyl) (trimethylsilylbenzyl) and the like; (bridged-cyclopentadienyl)zirconium compounds such as methylene bis(cyclopentadienyl)zirconium dimethyl, methylene(cyclopentadienyl)zirconium dimethyl, ethylene bis(cyclopentadienyl)zirconium dimethyl, dimethylsilyl bis(cyclopentadienyl)zirconium dihydride, ethylene bis(cyclopentadienyl)zirconium dihydride and dimethylsilyl bis(cyclopentadienyl)zirconium dihydride and the like; chiral and C₂-symmetry compounds; "zirconacycles": asymmetrically bridged-dicyclopentadienyl compounds such as methylene(cyclopentadienyl)(1-fluoroenyl)zirconium dimethyl, dimethylsily(cyclopentadienyl)(1-fluorenyl)zirconium dihydride, isopropyl(cyclopentadienyl)(1-fluorenyl)zirconium dimethyl, isopropyl(cyclopentadienyl)1-octahydrofluorenyl)zirconium dimethyl, dimethylsil)(methylcyclopentadienyl)(1-fluoroenyl)zirconium dihydride, methylene(cyclopentadienyl(tetramethylcyclopentadienyl)zirconium dimethyl and the like: racemic and meso isomers of symmetrically bridged substituted dicyclopentadienyl compounds such as ethylenebis(indenyl)zirconium dimethyl, dimethylsilylbis(indenyl)zirconium dimethyl, ethylenebis(tetrahydroindenyl)zirconium dimethyl, dimethylsilylbis(3-trimethylsilylcyclopentadienyl)zirconium dihydride and the like;

zirconacycles such as bis(pentamethylcyclopentadienyl) zirconacyclobutane, bis(pentamethylcyclopentadienyl) zirconacyclopentane, bis(cyclopentadienyl)zirconaindane, 1-bis(cyclopentadienyl)zirconia-3-dimethylsila-cyclobutane and the like; olefin, diolefin and aryne ligand substituted bis(cyclopentadienyl)zirconium compounds such as bis(cyclopentadienyl) (1,3-butadiene)zirconium, bis(cyclopentadienyl) (2,3-dimethyl-1,3-butadiene)zirconium, bis(pentamethylcyclopentadienyl)(benzene)zirconium and the like; (hydrocarbyl)(hydride) bis(cyclopentadienyl)zirconium compounds such as bis(pentamethylcyclopentadienyl)zirconium (phenyl)(hydride), bis(pentamethylcyclopentadienyl)zirconium (methyl)(hydride) and the like; and bis(cyclopentadienyl) zirconium compounds in which a substituted on the cyclopentadienyl radical is bound to the metal such as (pentamethylcyclopentadienyl) (tetramethylcyclopentadienylmethylene) zirconium hydride, (pentamethylcyclopentadienyl) (tetramethylcyclopentadienylmethylne)zirconium phenyl and the like.

A similar list of illustrative bis(cyclopentadienyl) hafnium and bis(cyclopentadienyl)titanium compounds could be made, but since the lists would be nearly identical to that already presented with respect to bis(cyclopentadienyl)zirconium compounds, such lists are not deemed essential to a complete disclosure. Other bis(cyclopentadienyl)hafnium compounds and other bis(cyclopentadienyl)titanium compounds as well as other bis(cyclopentadienyl)zirconium compounds which are useful in the catalyst compositions of this invention will, of course, be apparent to those skilled in the art.

B. The Activator Component

Compounds useful as an activator component in the preparation of the catalyst of this invention will comprise a cation, which is a Bronsted acid capable of donating a proton or which will irreversibly react with at least one ligand contained in the Group IV-B metal compound and a compatible noncoordinating anion which anion is relatively large (bulky), capable of stabilizing the active catalyst species (the Group IV-B cation) which is formed when the two compounds are combined and said anion will be sufficiently labile to e displaced by olefinic, diolefinic and acetylenically unsaturated substrates or other neutral Lewis bases such as ethers, nitriles and the like. Two classes of compatible non-coordinating anions have been disclosed in European Patent Applications 277,003 and 277,004: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In general, the activator compounds containing single anionic coordination complexes which are useful in this invention may be represented by the following general formula:

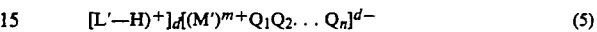

$$[L'{-}H]^+{}_d[(M')^{m+}Q_1Q_2\ldots Q_n]^{d-} \quad (5)$$

wherein:
L' is a neutral Lewis base;
H is a hydrogen atom;
[L'—H] is a Bronsted acid;
M' is a metal or metalloid selected from the Groups subtended by Groups V-B to V-A of the Periodic Table of the Elements; i.e., Groups V-B, VI-B, VII-B, VIII, I-B, II-B, III-A, IV-A, and V-A;
$Q_1$ to $Q_n$ are selected, independently, from the Group consisting of hydride radicals, dialkylamido radicals, alkoxide and aryloxide radicals, hydrocarbyl and substituted-hydrocarbyl radicals and organometalloid radicals and any one, but not more than one, of $Q_1$ to $Q_n$ may be a halide radical, the remaining $Q_1$ to $Q_n$ being, independently, selected from the foregoing radicals;
m is an integer from 1 to 7;
n is an integer from 2 to 8; and n−m=d.

As indicated above, any metal or metalloid capable of forming an anionic complex which is stable in water may be used or contained in the anion of the second compound. Suitable metals, then, include, but are not limited to, aluminum, gold, platinum and the like. Suitable metalloids include, but are not limited to, boron, phosphorus, silicon and the like. Compounds containing anions which comprise coordination complexes containing a single metal or metalloid atom are, of course, well known and many, particularly such compounds containing a single boron atom in the anion portion, are available commercially. In light of this, salts containing anions comprising a coordination complex containing a single boron atom are preferred.

The preferred activator compounds comprising boron may be represented by the following general formula:

$$[L'H]^+[BAr_1Ar_2X_3X_4]^- \quad (5A)$$

wherein
L' is a neutral Lewis base;
H is a hydrogen atom;
[L'—H]⁺ is a Bronsted acid;
B is boron in a valence state of 3;
$Ar_1$ and $Ar_2$ are the same or different aromatic or substituted-aromatic hydrocarbon radicals containing from about 6 to about 20 carbon atoms and may be linked to each other through a stable bridging group; and
$X_3$ and $X_4$ are radicals selected, independently, from the group consisting of hydride radicals, halide radicals, with the proviso that $X_3$ and $X_4$ will not be halide at the same time, hydrocarbyl radicals containing from 1 to about 20 carbon atoms, substituted-hydrocarbyl radicals, wherein one or more of the hydrogen atoms is replaced by a halogen atom, containing from 1 to about 20 carbon atoms, hydrocarbyl-substituted metal (organometalloid) radicals wherein each hydrocarbyl substitution contains from 1 to about 20 carbon atoms, hydrocarbyl-substituted metal (organometalloid) radicals wherein each hydrocarbyl substitution contains from 1 to about 20 carbon atoms and said metal is selected from Group IV-A of the Periodic Table of the Elements and the like.

In general, $Ar_1$ and $Ar_2$ may, independently, be any aromatic or substituted-aromatic hydrocarbon radical containing from about 6 to about 20 carbon atoms. Suitable aromatic radicals include, but are not limited to, phenyl, naphthyl and anthracenyl radicals. Suitable substituents on the substituted-aromatic hydrocarbon radicals, include, but are not necessarily limited to, hydrocarbyl radicals, organometalloid radicals, alkoxy radicals, alkylamido radicals, fluoro and fluorohydrocarbyl radicals and the like such as those useful as $X_3$ and $X_4$. The substituent may be ortho, meta or para, relative to the carbon atoms bonded to the boron atom. When either or both $X_3$ and $X_4$ are a hydrocarbyl radical, each may be the same or a different aromatic or substituted-aromatic radical as are $Ar_1$ and $Ar_2$, or the same way be a straight or branched alkyl, alkenyl or alkynyl radical having from 1 to about 20 carbon atoms, a cyclic hydrocarbon radical having from about 5 to about 8 carbon atoms or an alkyl-substituted cyclic hydrocarbon radical having from about 6 to about 20 carbon atoms. $X_3$ and $X_4$ may also, independently, be alkoxy or dialkylamido radicals wherein the alkyl portion of said alkoxy and dialkylamido radicals contain from 1 to about 20 carbon atoms, hydrocarbyl radicals and organometalloid radicals having from 1 to about 20 carbon atoms and the like. As indicated above, $Ar_1$ and $Ar_2$ may be linked to each other. Similarly, either or both of $Ar_1$ and $Ar_2$ could be linked to either $X_3$ or $X_4$. Finally, $X_3$ or $X_4$ may also be linked to each other through a suitable bridging group.

Illustrative, but not limiting, examples of boron compounds which may be used as an activator component in the preparation of the improved catalysts of this invention are trialkyl-substituted ammonium salts such as triethylammonium tetra(phenyl)boron, tripropylammonium tetra(phenyl)boron, tri(n-butyl)ammonium tetra(phenyl)boron, trimethylammonium tetra(p-tolyl)boron, trimethylammonium tetra(o-toly)boron, tributylammonium tetra(pentafluorophenyl)boron, tripropylammonium tetra(o,p-dimethylphenyl)boron, tributylammonium tetra(m,m-dimethylphenyl)boron, tributylammonium tetra(p-tri-fluoromethylphenyl)boron, tri(n-butyl)ammonium tetra(o-tolyl)boron and the like; N,N-dialkyl anilinium salts such as N,N-dimethylanilinium tetra(pentafluoro phenyl)boron, N,N-diethylanilinium tetra(phenyl)boron, N,N-2,4,6-pentamethylanilinium tetra(phenyl)boron and the like; dialkyl ammonium salts such as di(i-propyl)ammonium tetra(pentafluorophenyl)boron, dicyclohexylammonium tetra(phenyl)boron and the like; and triaryl phosphonium salts such as triphenylphosphonium tetra(phenyl)boron, tri(methylphenyl)phosphonium tetra(phenyl)boron, tri(dimethylphenyl)phosphonium tetra(phenyl)boron and the like.

Similar lists of suitable compounds containing other metals and metalloids which are useful as activator components may be made, but such lists are not deemed necessary to a complete disclosure. In this regard, it should be noted that the foregoing list is not intended to be exhaustive and that other useful boron compounds as well as useful compounds containing other metals or metalloids would be readily apparent to those skilled in the art from the foregoing general equations.

Activator components based on anions which contain a plurality of boron atoms may be represented by the following general formulae:

$$[L'-H]_d[(CX)_a(M''X')_mX']_b]^{c-} \qquad (6)$$

$$[L'-H]_d[[(CX_3)_{a'}(M''X_4)_{m'}(X_5)_{b'}]^{c'-}]_2M^{n+}]^{d-} \qquad (7)$$

wherein $[L'-H]$ is either $H^+$, ammonium or a substituted ammonium cation having up to 3 hydrogen atoms replaced with a hydrocarbyl radical containing from 1 to about 20 carbon atoms or a substituted-hydrocarbyl radical, wherein one or more of the hydrogen atoms is replaced by a halogen atom, containing from about 1 to about 20 carbon atoms, phosphonium radicals, substituted-phosphonium radicals having up to 3 hydrogen atoms replaced with a hydrocarbyl radical containing from 1 to about 20 carbon atoms or a substituted-hydrocarbyl radical, wherein 1 or more of the hydrogen atoms is replaced by a halogen atom, containing from 1 to about 20 carbon atoms and the like; C is carbon; $M''$ is boron or phosphorus; each of X, X', X'', $X_3X_4$ and $X_5$ are radicals selected, independently, from the group consisting of hydride radicals, halide radicals, hydrocarbyl radicals containing from 1 to about 20 carbon atoms, substituted-hydrocarbyl radicals, wherein one or more of the hydrogen atoms is replaced by a halogen atom, containing from 1 to 20 carbon atoms, organometalloid radicals wherein each hydrocarbyl substitution in the organo portion contains from 1 to about 20 carbon atoms and said metal is selected from Group IV-A of the Periodic Table of the Elements and the like; M is a transitional metal; "a" and "b" are integers $>0$; "c" is an integer $>1$; $a+b+c=$ an even-numbered integer from 2 to about 8; and "m" is an integer ranging from 5 to about 22; "a'" and "b'" are the same or a different integer $>0$; "c'" is an integer $>2$; $a'+b'+c'=$ an even-numbered integer from 4 to about 8; "m'" is an integer from 6 to about 12; "n" is an integer such that $2c'-n=d$; and "d" is an integer greater than or equal to 1.

Illustrative, but not limiting, examples of second components which can be used in preparing catalyst system utilized in the process of this invention wherein the anion of the second component contains a plurality of metalloid atoms (as in formulae 5 and 6) are ammonium salts such as ammonium 1-carbadodecaborate (using 1-carbadodecarborate as an illustrative, but not limiting, counterion for the ammonium cations listed below): monohydrocarbyl-substituted ammonium salts such as methylammonium 1-carbadodecaborate, ethylammonium 1-carbadodecaborate, propylammonium 1-carbadodecaborate, isopropylammonium 1-carbadodecaborate, (n-butyl)ammonium 1-carbadodecaborate, anilinium 1-carbadodecaborate, and (p-tolyl)ammonium 1-carbadodecaborate and the like; dihydrocarbyl-substituted ammonium salts such as dimethylammonium 1-carbadodecaborate, diethylammonium 1-carbadodecaborate, dipropylammonium 1-carbadodecaborate, diisopropylammonium 1-carbadodecaborate, di(n-butyl) ammonium 1-carbadodecaborate, diphenylammonium 1-carbadodecaborate, di(p-tolyl)ammonium 1-carbabodecaborate and the like; trihydrocarbyl-substituted ammonium salts such as trimethylammonium 1-carbodedecaborate, triethylammonium 1-carbadodecaborate, tripropyl-ammonium 1-carbadodecaborate, tri(n-butyl) ammonium 1-carbadodecaborate, triphenylammonium 1-carbadodecaborate, tri(p-tolyl)ammonium 1-carbadodecaborate, N,N-dimethylaniliniuj 1-carbadodecaborate, N,N-diethylanilinium 1-carbadodecaborate and the like.

Illustrative, but not limiting examples of second compounds corresponding to Formula 5 [using tri(n-butyl)ammonium as an illustrative, but not limiting, counter-ion for the anions listed below] are salts of anions such as bis[tri(n-butyl)ammonium] monaborate, bis[tri(n-butyl)ammonium]decaborate, bis[tri(n-butyl) ammonium]undecaborate, bis[tri(n-butyl)ammonium] dodecaborate, bis[tri(n-butyl)ammonium]decachlorodecaborate, tri(n-butyl)ammonium dodecachlorododecaborate, tri(n-butyl)ammonium 1-carbadecaborate, tri(n-butyl) ammonium 1-carbaundecaborate, tri(n-butyl)ammonium 1-carbadodecaborate, tri(n-butyl)ammonium 1-trimethylsilyl-1-carbadecaborate, tri(n-butyl)ammonium dibromo-1-carbadodecaborate and the like; borane and carborane complexes and salts of borane and carborane anions such as decaborane(14), 7,8-dicarbaundecaborane(13), 2,7-dicarbaundecaborane(13), undecahydrido-7,8-dimethyl-7,8-dicarbaundecaborane, dodecahydrido-11-methyl1-2,7-di-carbaundecaborane, tri(n-butyl) ammonium undecaborate(14), tri(n-butyl)ammonium 6-carbadecaborate(12), tri(n-butyl)ammonium 7-carbaundecaborate(13), tri(n-butyl)ammonium 7,8-dicarbaundecaborate(12), tri(n-butyl)ammonium 2,9-dicarbaundecaborate(12), tri(n-butyl)ammonium dodecahydrido-8-methyl-7,9-dicarbaundecaborate(12), tri(n-butyl)ammonium undecahydrido-8-ethyl-7,9-dicarbaundecaborate(12), tri(n-butyl)ammonium undecahydrido-8-butyl-7,9-dicarbaundecaborate(12), tri(n-butyl)ammonium undecahydrido-8-allyl-7,9-dicarbaundecaborate(12), tri(n-butyl)ammonium undecahydrido-8-trimethylsilyl-7,8-dicarbaundecaborate, tri(n-butyl)ammonium undecahydrido-4,6-dibromo-7-carbaundecaborate and the like; boranes and carboranes and salts of boranes and carboranes such as 4-carbanonaborane(14), 1,3-dicarbanonaborane(13), 6,9-dicarbadecaborane(14), dodecahydrido-1-phenyl-1,3-dicarbanonaborane, dodecahydrido-1-methyl-1,3-dicarbanonaborane, dodecahydrido-1,3-dimethyl-1,3-dicarbanonaborane and the like.

Illustrative, but not limiting, examples of second compounds corresponding to Formula 7 [using tri(n-butyl)ammonium as an illustrative, but not limiting, counter-ion for the anions listed below] are salts of metallacarborane and metallaborane anions such as tri(n-butyl)ammonium bis(nonahydrido-1,3-dicarbanonaborato) cobaltate(III), tri(n-butyl)ammonium bis(undecahydrido-7,8-dicarbaundecaboratoferrate(III), tri(n-butyl) ammonium bis(undecahydrido-7,8-dicarbaunaborato)cobaltate(III), tri(n-butyl)ammonium bis(undecahydrido-7,8-dicarbaunaborato) nickelate(III), tri(n-butyl)ammonium bis(nonahydrido-7, 8-dimethyl-7,8-dicarbaundecaborato)ferrate(III), tri(n-butyl)ammonium bis(nonahydrido-7,8-dimethyl-7,8-dicarbaundecaborato)chromate(III), tri(n-butyl)ammonium bis(-tribromooctahydrido-7,8-dicarbaundecaborato)cobaltate(III), tri(n-butyl)ammonium bis(dodecahydridodicarbadodecaborato) cobaltate(III), tris[tri(n-butyl)ammonium] bis (undecahydrido-7-carvaundecaborato)chromate(III), bis[tri(n-butyl) ammonium] bis(undecahydrido-7-carbaundecaborato)manganate(IV), bis[tri(n-butyl)ammonium] bis(undecahydrido-7-carbaundecaborato) cobaltate(III), and the like. A similar list of representative phosphonium compounds can be recited as illustrative second compounds, but for the sake of brevity, it is simply noted that the phosphonium and substituted-phosphonium salts corresponding to the listed ammonium and substituted-ammonium salts could be used as second compounds in the present invention.

CHOICE OF METALLOCENE-ACTIVATOR PAIRS

In general, and while most metallocene components identified above may be combined with most activator components identified above to produce an active olefin polymerization catalyst, it is important for continuity of the polymerization operatons that either the metal cation initially formed from the metallocene component or a decomposition product thereof be a relatively stable catalyst. It is also important that the anion of the activator compound be stable to hydrolysis when an ammonium salt is used. Further, it is important that the acidity of the activator component be sufficient, relative to the metallocene component, to facilitate the needed proton transfer or reaction between a ligand of the metallocene compound with the cation of the second component. Activator compounds containing aryl-ammonium salts such as N,N-dimethylanilinium are more acid than trialkylammonium salts and therefore are useful with a wider variety of metallocene components. The basicity of the metal complex must also be sufficient to facilitate the needed proton transfer. In general, bis(cyclopentadienyl)metal compounds which can be hydrolyzed by aqueous solutions can be considered suitable as metallocene components to form the catalysts described herein.

The chemical reactions which occur may be represented by reference to the general formulae set forth herein as follows:

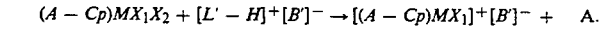
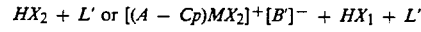
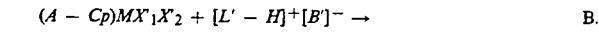
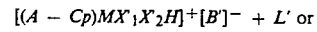
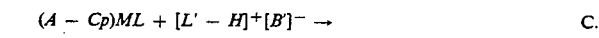
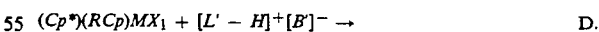
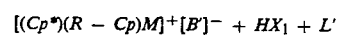

In the foregoing reaction equations, the letters A-D correspond to the numbers 1-4, respectively, set forth in combination with the general equations for useful metallocene compounds. B' represents a compatible ion corresponding to the general formulae outlined in formulae 5, 6 and 7 above. When the metallocene and activator components used to prepare the improved catalysts of the present invention are combined in a suitable solvent or diluent, all or a part of the cation of the activator (the acidic proton) combines with one of the substituents on the metallocene compound. In the case where the metallocene component has a formula corresponding to that of general formula 1, a neutral compound is liberated, which neutral compound either remains in solution or is liberated as a gas. In this regard, it should be noted that if either $X_1$ or $X_2$ in the metallocene component is a hydride, hydrogen gas may be liberated. Similarly, if either $X_1$ or $X_2$ is a methyl radical, methane may be liberated as a gas. In the cases where the first component has a formula corresponding to those of general formulae 2, 3 or 4 (optional), one of the substituents on the metallocene component is protonated but no substituent is liberated. In general, the stability and rate of formation of the products in the foregoing reaction equations will vary depending upon the choice of the solvent, the acidity of the $[L'—H]^+$ selected, the particular $L'$, the anion, the temperature at which the reaction is completed and the particular cyclopentadienyl derivative of the metal selected.

With respect to the combination of the metallocene component with the activator component to form a catalyst of this invention, it should be noted that the two compounds combined for preparation of the active catalyst must be selected so as to avoid transfer of a fragment of the anion to the metal cation, thereby forming a catalytically inactive species. This could be done by steric hindrance, resulting from substitutions of the cyclopentadienyl carbon atoms as well as substitutions of the non-coordinating anion.

It follows, then, that the metallocene components comprising perhydrocarbyl-substituted cyclopentadienyl radicals could be effectively used with a broader range of activator compounds than could metallocene components comprising unsubstituted cyclopentadienyl radicals.

As the amount and size of the substitutions on the cyclopentadienyl radicals are reduce, however, more effective catalysts are obtained with activator compounds containing non-coordinating anions which are larger in size and more resistant to degradation. In the case where the non-coordinating anion is an anionic coordination complex, such as a tetraphenylboron derivative, substitutions on the phenyl rings can be used to prevent the transfer of a proton or an entire phenyl group from the anion to the metal. This can be accomplished by alkyl substitution in the ortho positions of the phenyl groups, or, more preferably, by perfluoro-substitutions on the anion. Thus, anionic coordination complexes containing perfluorphenyl-, trifluoromethylphenyl-, or bis-trifluoromethylphenyl rings are preferred to this subgenus of activator components. When the non-coordinating anion contains a plurality of boron atoms as described in general formulae 6 and 7, more effective catalysts are obtained with activator compounds containing larger anions, such as those encompassed by Equation 7 and those having larger m values in Equation 6. In these cases it is further preferable when using second compounds which are encompassed by Equation 6, that $a+b'c=2$. Second compounds in which $a+b+c=$ even-numbered integers of 4 or more have acidic B-H-B moieties which can react further with the metal cation formed, leading to catalytically inactive compounds.

As indicated supra, most metallocene compounds will combine with most activator compounds to give an active polymerization catalyst. The initially formed catalyst is not, however, always sufficiently stable as to permit its separation and subsequent identification. However, catalysts which are thermally stable are preferred. Three structurally distinct forms of thermally stable ionic catalysts have been identified by NMR spectroscopy and are shown below in equation 8.

$$[A—CpMX_1][(C_2B_9H_{11})_2Co] \tag{8a}$$

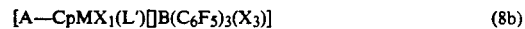
$$[A—CpMX_1(L')][B(C_6F_5)_3(X_3)] \tag{8b}$$

$$[(A—CpMX_1)_2X_1][B'] \tag{8c}$$

In the foregoing reactions the symbols A—Cp, M, $X_1$, $L'$ and $X_3$ correspond to the definitions set forth in equations 1-4 and 5-5a, respectively; $B'$ represents a compatible non-coordinating anion corresponding to the general formulae set forth in equations 5, 6 and 7. In example 8a, NMR spectroscopy indicates that the metallocarborane anion is weakly bound to the metal center; the byproduct $L'$ does not form an observable coordination complex with the metallocene center. In 8b, NMR experiments indicate that the fluorinated boron anion is completely non-coordinating and that $L'$, weakly coordinates to and stabilizes the metallocene cation when the tertiary amine ($L'$) is an aniline derivative. The ability of $L'$ to coordinate to the metal is important to the stability of the catalyst systems which have highly noncoordinating anions. The Lewis basicity of the $L'$ can affect the rate of polymerization and other polymerization parameters. Experience has shown that when the bulk of the amine of the metallocene cation is increased by substitutions on the nitrogen atom or the cyclopentadienyl ligands respectively, the ability for the amine to coordinate to the metal center decreases. Addition of excess metallocene $ACpM(X_1)_2$ to 8a or 8b results in displacement of the anion in 8a or the aniline ligand in 8b to form a stable dimeric cation 8c.

While in general, organometallic complexes which are reactive towards oxygen, water, and similar impurities and which do not release polar groups—such as halides or oxygenates—which can irreversibly coordinate to the catalyst active site, preferred additive compounds are organometallic complexes of the Group III-A element represented by the following general formula:

Group III-A additive compounds suitable for use in preparing catalyst systems of the invention are represented by the following general formula:

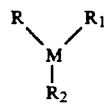

wherein, M is a Group III-A element, preferably aluminum and boron; R, $R_1$ and $R_2$ are, independently, a straight or branched chain alkyl radical, a cyclic hyrocarbyl radical, an alkyl-substituted cyclohydrocarbyl radical, an aromatic radical or an alkyl-substituted radical of $C_1$ to $C_{20}$ in carbon number. $R_2$ may also be an alkoxide radical of $C_1$ to $C_{20}$ in carbon number.

Illustrative, but non-limiting, examples of Group III-A element compounds which are suitable are: when M is aluminum (Al) the trialkyl aluminums such as trimethyl aluminum, triethyl aluminum, tri-n-propyl aluminum tri-isopropyl aluminum, tri-n-butyl aluminum, tri-sec-butyl aluminum, tri-t-butyl aluminum, tri-isobutyl aluminum, tri-n-pentyl aluminum, tri-isopentyl aluminum, tri-neopentyl aluminum, tricyclopentyl aluminum, tri-n-hexyl aluminum, tri-(4-methylphenyl) aluminum, tri-(3-methylphenyl) aluminum, tricyclohexyl aluminum, and the like; alkyl aluminums such as dimethylethyl aluminum, methyldiethyl aluminum, ethyldimethyl aluminum, dimethyl-n-propyl aluminum, methyldi-n-propyl aluminum, dimethylisopropyl aluminum, dimethylcyclohexyl aluminum, methylethylpropyl aluminum, and the like, aryl and alkyl-substituted aluminums, such as triphenyl aluminum, tri-p-tolyl aluminum, tri-m-tolyl aluminum, tri-p-ethyl aluminum, and the like. Also suitable are aluminum alkoxides and aryloxides such as dimethyl aluminum methoxide, dimethyl aluminum ethoxide, diethyl aluminum ethoxide, diethyl aluminum isopropoxide, methyl ethyl aluminum methoxide, dimethyl aluminum 4-methylphenoxide, demethyl aluminum 3-methylphenoxide, dimethyl aluminum 2,6-diisopropylphenoxide, dimethyl aluminum 2,6-di-t-butyl-4-methylphenoxide, and the like.

A similar list of illustrative Group III-A element compounds when M is boron could be made for the trialkyl boranes, alkyl boranes, and alkyl borane alkoxides. Also a similar list could be given for the analogous compound of gallium and indium. Such list would be nearly identical to that already presented with respect to the aluminum species of Group III-A element compounds and therefore such listing of the borone analogues and other III-A elements analogues are not necessary to a complete disclosure.

Preferred Group III-A element compounds are those where M is aluminum or boron. Of the aluminum species of Group III-A element compounds, the most preferred are trialkylaluminums, and of the trialkylaluminums the most preferred are triethylaluminum and trimethylaluminum. Of the group II-A element compounds wherein M is boron, the preferred boron species of Group III-A element compounds are trialkylboranes of which the most preferred is triethylborane.

POLYMERIZATION PROCESS

The process of this invention is one which polymerizes olefins, diolefins, cyclic olefins, and acetylenically unsaturated monomers to provide polyolefine homo and copolymers of narrow molecular weight distribution and higher weight average molecular weights than that heretofore attainable with a metallocene activated to an active catalyst species by an alkyl aluminum or alumoxane cocatalyst. The process of this invention obtains such high molecular weight polyolefins at a rate of ionic metallocene catalyst productivity which is substantially greater than heretofore observed for a system of ionic metallocene catalyst.

The catalysts of this invention can be employed in gas phase polymerization process, solution polymerization process, including high pressure and bulk monomer polymerization processes. In a gas phase process the ionic catalyst would be desirably supported as described in copending U.S. application 459,921, filed Jan. 2, 1990.

A preferred polymerization process is bulk monomer or solution, including high pressure processes, comprises the steps of: (1) contacting one or more monomers in a polymerization diluent with the ionic metallocene catalyst and additive compound; (2) continuing the contact of such monomer with such catalyst system for a time sufficient to polymerize at least a portion of such monomer; and (3) recovering a polymer product.

In a preferred embodiment of the present invention, a bis(cyclopentadienyl)-Group IV-B metal compound containing two, independently, substituted or unsubstituted cyclopentadienyl radicals and one or two lower alkyl substituents and/or one or two hydride substituents will be combined with a tri-substituted ammonium salt of either a substituted or unsubstituted tetra(aromatic)boron. Each of the tri-substitutions in the ammonium cation will be the same or a different lower alkyl or aryl radical. By lower alkyl is meant an alkyl radical containing from 1 to 4 carbon atoms. When the bis(cyclopentadienyl)metal compound used is a bis(perhydrocarbyl-substituted cyclopentadienyl)metal compound, an unsubstituted or partially substituted tetra(aromatic)boron salt may be used. Tri(n-butyl)ammonium tetra(phenyl)boron, tri(n-butyl)ammonium tetra(p-tolyl)boron and tri(n-butyl)ammonium tetra(p-ethylphenyl)boron are particularly preferred. As the number of hydrocarbyl-substitutions on the cyclopentadienyl radicals is reduced, however, substituted anions will be used in the tri-substituted ammonium salts, particularly, pentafluoro-substituted anions. N,N-dimethylanilinium tetra(fluorophenyl)boron is particularly preferred.

Certain of the catalysts of this invention, particularly those based on a hafnocenes—using the catalyst produced from the reaction of bis(cyclopentadienyl)hafnium dimethyl and the tri-substituted ammonium salt of tetra(pentafluorophenyl)boron as an example—when used as described herein for the polymerization and copolymerization of α-olefins, diolefins, and/or acetylenically unsaturated monomers, in the absence of a chain transfer agent, can lead to the production of extremely high molecular weight polymers and copolymers having relatively narrow molecular weight distributions. In this regard, it should be noted that homopolymers and copolymers having molecular weight up to about $2 \times 10^6$ or higher and molecular weight distributions within the range of about 1.5 to about 15 can be produced with the catalysts of this invention.

The ionic metallocene catalysts containing a metallocene component which is either a pure enantiomer or the racemic mixture of two enantionmers of a rigid, chiral metallocene can polymerize prochiral olefins (propylene and higher α-olefins) to isotactic polymers. Bis(cyclopentadienyl)metal compounds in which each of the cyclopentadienyl radicals is substituted and containing a covalent bridging group between the two cyclopentadienyl radicals are particularly useful for isotactic polymerization of this type. Prochiral metallocenes, for example these based on complexes of isopropyl-2-cyclopentadienyl-2-(1-fluorenyl) hafnium, can be used to polymerize propylene or higher α-olefins to syndiotactic polymers.

A particularly surprising feature of some of the ionic metallocene catalysts, particularly those based on hafnocenes in combination with an activator component comprising perfluorinated tetraphenylborate anions, is that when these catalysts are used to copolymerize α-olefins, either alone or in combination with diolefins, the amount of higher molecular weight olefin or diolefin incorporated into the copolymer is significantly increased when compared to copolymers prepared with the more conventional Ziegler-Natta type catalysts and bis(cyclopentadienyl)zirconium catalysts. The relative rates of reaction of ethylene and higher α-olefins with the aforementioned hafnium-based catalysts of this invention are much closer than with conventional Ziegler-Natta type catalysts of the Group IV-B metals. The comonomer distribution in copolymers prepared with the ionic metallocene catalysts, particularly with the lower α-olefins and lower diolefins, will range from near perfectly alternating to statistically random. Consequently, the hafnocene based ionic metallocene catalysts are particularly preferred.

While the ionic metallocene catalysts do not contain pyrophoric species, it is nevertheless preferred that the catalyst components be handled in an inert, moisture-free, oxygen-free environment such as argon, nitrogen, or helium because of the sensitivity of the catalyst components to moisture and oxygen. The Group III-A element compounds must also be handled in a similar manner.

In the preferred method, the metallocene and activator components are combined in a first step in an aromatic solvent to produce a solution of the ionic metallocene catalyst. This reaction may be carried out in the temperature range of about $-100°$ C. to about $300°$ C., preferably about $0°$ to about $100°$ C. Holding times to allow for the completion of the reaction may range from about 10 seconds to about 60 minutes depending upon variables such as reaction temperature and choice of reactants.

Once the ionic metallocene catalyst component is formed, the order or method of addition of the additive element compound to the polymerization diluent with ionic metallocene catalyst is not critical. That is, the catalyst system may be formed by: 1) first adding the additive compound to the polymerization diluent followed by addition of the ionic metallocene catalyst; 2) direct addition of the additive compound to a solution of ionic metallocene catalyst after which the common solution is added to a polymerization diluent; or 3) a portion of the additive compound may be added to a liquid monomer and supplied to the polymerization diluent containing ionic metallocene catalysts as the liquid monomer is supplied to the diluent. When a liquid monomer is used in the polymerization process, it is preferred to add the additive compound to the liquid monomer. The additive may be added neat or as a solution in a suitable hydrocarbon solvent, preferably an aliphatic or aromatic solvent.

The use of too great or too small an amount of additive compound in forming a catalyst system of the invention will result in a decrease of the advantages of this invention. The optimum amount of additive compound for use in producing catalyst systems of the invention is dependent, in part upon the amount of undesirable impurities contained in the polymerization diluent and/or monomers. In a typical polymerization process, it is expected that the optimum amount of additive compound to be added to obtain a catalyst system of maximum productivity will amount to a mole ratio of additive compound to catalyst of from about 0.1:1 to about 200:1, preferably 1:1 to 150:1.

For a given polymerization process, the optimum amount of additive compound to be added to a polymerization diluent in which an ionic metallocene catalyst component is present for forming a catalyst system of enhanced activity may readily be determined by monitoring the level of monomer consumption while adding the additive compound to the polymerization diluent until an amount of additive compound has been added which maximizes the rate at which the monitored monomer is consumed in the polymerization reaction. Alternatively, a portion of the additive compound is first added to the polymerization diluent after which the ionic metallocene catalyst is added and polymerization is initiated and the rate of monomer consumption is monitored, Then, while polymerization is ongoing, an additional quantity of the additive compound is added and the consumption is observed. It should, however, be borne in mind that the objective of adding the additive is to neutralize adventitious impurities such as water or oxygen so that the level of additive addition should also be proportioned to the level of impurities present. Thus, it may be advantageous to pretreat a monomer having a relatively high level of such impurities with the additive before the monomer is brought into contact with the catalyst system.

In general, the catalyst systems of this invention will polymerize olefins, diolefins and/or acetylenically unsaturated monomers either alone or in combination with other olefins and/or other unsaturated monomers at conditions well known in the prior art for conventional Ziegler-Natta catalysts.

Monomers which may be used in practice of the process include α-olefins, diolefins, and acetylenically unsaturated hydrocarbons containing from about 2 to about 18 carbon atoms. Such monomers include cyclic and acyclic hydrocarbons, and straight or branched chain hydrocarbons. Illustrative, and not limiting, of suitable monomers are: ethylene, propylene, 1-butene, 1-pentene, 1-hexane, 1-octene, 1-decene and the like; 2-methyl-1-propene, 3-methyl-1-butene, 2-methyl-1-butene, 3-methyl-1-pentene, 4-methyl-1-pentene, and the like; 1,3-butadiene, 1,4-pentadiene, 1,5-hexadiene, 1,4-hexadiene and the like; cyclopentene, cyclohexene, cycloheptane, and the like; propyne, butadyne, 1-4-hexadyne and the like.

In a most preferred embodiment of the present invention, bis(cyclopentadienyl)zirconium dimethyl or bis(cyclopentadienyl)hafnium dimethyl is reacted with N,N-dimethylanilinium tetra(pentafluorophenyl)boron to produce the most preferred ionic metallocene catalyst. The metallocene and activator are combined at a temperature within the range from about $0°$ C. to about $100°$ C., preferably in an aromatic hydrocarbon solvent, most preferably toluene. Nominal holding times within the range from about 10 seconds to about 60 minutes are sufficient to produce the preferred ionic metallocene catalyst. The ionic metallocene catalyst is thereafter added to a polymerization diluent to which a Group III-A element compound, preferably triethylaluminum or triethylboron, has previously been added. The catalyst system so resulting is then, immediately after formation, used to polymerize a lower α-olefin, particularly ethylene or propylene, most preferably ethylene, at a temperature within the range from about $0°$ C. to about $100°$ C., more preferably at from about $25°$ to $100°$ C., and at a pressure within the range from about 15 to about 500 psig. In a most preferred embodiment of the present invention, the most preferred catalyst system is used either to homopolymerize ethylene or to copolymerize ethylene with a lower α-olefin having from 3 to 6 carbon atoms, thereby yielding a plastic or an elastomeric copolymer. In both preferred process embodiments, the monomers are maintained at polymerization conditions for a nominal holding time within the range from about 1 to about 60 minutes and the system is within the range from about $10^{-6}$ to about $10^{-5}$ moles of Group IV-B metal per liter of polymerization diluent, while a mole ratio of the Group III-A element compound to activator compound employed is maintained at from about 15:1 to about 150:1.

The following examples serve to illustrate the invention and some of its advantages and are not intended to limit the scope of the invention as disclosed above or claimed hereafter.

EXAMPLES

Example 1

Ethylene was polymerized in a hexane diluent. Dry, oxygen-free hexane (400 ml) was added to a 1 liter stainless-steel autoclave previously flushed with nitrogen. Under nitrogen, a toluene solution (20 ml) containing 0.2 moles of triethylborane was transferred into the autoclave by means of a double-ended needle, followed by a solution of bis(cyclopentadienyl)zirconium dimethyl (3 mg) and N,N-dimethylanilinium tetrakis(pentafluorophenyl)boron (1.5 mg) in toluene (5 ml). The autoclave was pressured with 90 psig of ethylene and stirred at 40° C. After 1 hour, the autoclave was vented and opened. The yield of linear polyethylene was 52.8 g. The polymer had a weight average molecular weight ($M_w$) of 449,000 with a molecular weight distribution (MWD) of 1.98. When the same procedure was followed except that no triethylborane was added, the yield of linear polyethylene was 13.3 g with a $M_w$ of 455,000 and a MWD of 2.04.

Example 2

The procedure of Example 1 was repeated with the exception that a toluene solution (5 ml) containing bis(cyclopentadienyl)hafnium dimethyl (4mg) and N,N-dimethylanilinium tetrakis(pentafluorophenyl)boron (1.5 mg) was used. The yield of linear polyethylene was 24.6 g with a $M_w$ of 1,424,000 and a MWD of 2.46. When the same procedure was followed except that no triethylborane was added, the yield of linear polyethylene was 3.5 g with a $M_w$ of 485,000 and a MWD of 2.10.

EXAMPLE 3

Ethylene was polymerized in a hexane diluent. Dry, oxygen-free hexane (400 ml) was added to a 1 liter stainless-steel autoclave previously flushed with nitrogen. Under nitrogen, a toluene solution (20 ml) containing 0.2 mmoles of triethylborane was transferred into the autoclave by means of a double-ended needle. A catalyst solution of bis(cyclopentadienyl)hafnium dimethyl (18 mg) and N,N-dimethylanilinium tetrakis(pentafluorophenyl)boron (6 mg) in toluene (20 ml) was then injected into the autoclave by nitrogen pressure. The autoclave was pressured with 90 psig of ethylene and stirred at 40° C. After 30 minutes, the autoclave was vented and opened. The yield of linear polyethylene was 28.7 g. When the same procedure was followed except that no triethylborane was used, the yield of linear polyethylene was 12.6 g.

Comparative Example 3a

The procedure of Example 3 was repeated with the exception that a toluene solution (10 ml) containing triethylborane (0.1 mmole) was injected into the reactor first, followed by a toluene solution (30 ml) containing the catalyst of Example 3 and triethylborane (0.1 mmole). The yield of linear polyethylene was 30.9 g.

Comparative Example 3b

The procedure of Example 3 was repeated with the exception that triethylborane (0.2 mmoles) was contacted with the catalyst solution of Example 3 and the mixture injected into the autoclave. The yield of linear polyethylene was 33.3 g.

Example 4

The procedure of Example 1 was repeated using 20 ml of a toluene solution containing triethylaluminum (0.2 mmoles), followed by 10 ml of toluene solution containing 3 mg of bis(cyclopentadienyl)zirconium dimethyl and 3 mg of N,N-dimethylanilinium tetrakis(pentafluorophenyl)boron. The yield of linear polyethylene was 56.0 g with a $M_w$ or 313,000 and a MWD of 2.52. When the same procedure was followed except that no triethylaluminum was added, the linear polyethylene yield was 9.2 g with a $M_w$ of 377,000 and a MWD of 2.54.

Example 5

The procedure of Example 4 was repeated with the exception that a toluene solution (20 ml) containing 3 mg bis(cyclopentadienyl)hafnium dimethyl and 6 mg of N,N-dimethylanilinium tetrakis(pentafluorophenyl)boron) was used. The yield of linear polyethylene was 7.8 g as compared to zero yield in the absence of triethylaluminum when the same procedure was followed.

Comparative Example 5a

The procedure of Example 5 was repeated with the exception that 36 mg of bis(cyclopentadienyl)hafnium dimethyl was used and the N,N-dimethylanilinium tetrakis(pentafluorophenyl)boron was omitted. No polyethylene was formed.

Example 6

The procedure of Example 1 was repeated using a toluene solution (20 ml) containing 0.2 mmole of tri-sec-butylborane, followed by 10 ml of a toluene solution containing 2 mg of bis(cyclopentadienyl)zirconium dimethyl and 6 mg of N,N-dimethylanilinium tetrakis(pentafluorophenyl)boron). The yield of linear polyethylene was 2.12 g. The polymer had a $M_2$ of 464,000 with a MWD of 2.08. When the same procedure was followed but no tri-sec-butylborane was added, the yield of linear polyethylene was 0.8 g with a $M_w$ of 509,000 and a MWD of 2.06.

Example 7

The procedure of Example 6 was repeated with the exception that a toluene solution (10 ml) containing 3 mg of bis(cyclopentadienyl)hafnium dimethyl and 6 mg of N,N-dimethylanilinium tetrakis(pentafluorophenyl)boron) was used. The temperature rose to 52° C. during the course of polymerization. The yield of linear polyethylene was 6.3 g. The polymer had a $M_w$ of 835,000 and a MWD of 1.62. When the same procedure was followed but no tri-sec-butylborane was added, the yield of linear polyethylene was 1.7 g with a $M_w$ of 884,000 and a MWD of 1.99.

Example 8

The procedure of Example 1 was repeated using a toluene solution (20 ml) containing 0.2 mmole trimethylaluminum, followed by a toluene solution (10 ml) containing 1 mg of bis(cyclopentadienyl)zirconium dimethyl and 3.5 mg of N,N-dimethylanilinium tetrakis(pentafluorophenyl)boron. The yield of linear polyethylene was 40.4 g as compared to trace quantities when the same procedure was followed in the absence of trimethylaluminum.

Example 9

The procedure of Example 1 was repeated using 2 ml of a solution containing 1 ml of a 25.4 wt. % solution of diethylaluminum ethoxide diluted to 20 ml with toluene, followed by 10 ml of a toluene solution containing 4 mg of bis(cyclopentadienyl)zirconium dimethyl and 12 mg of N,N-dimethylanilinium tetrakis(pentafluorophenyl)boron. The yield of linear polyethylene was 43 g as compared to no yield in the absence of diethylaluminum ethoxide when the same procedure was used.

Example 10

The procedure of Example 9 was repeated using a toluene solution (10 ml) containing 3 mg of bis(cyclopentadienyl)hafnium dimethyl and 6 mg of N,N-dimethylanilinium tetrakis(pentafluorophenyl)boron. The yield of linear polyethylene was 4.75 g. The $M_w$ of the polymer was 1,101,000 and the MWD was 1.55. When the same procedure was followed in the absence of diethylaluminum, the yield of linear polyethylene was 4.0 g with a $M_w$ of 899,000 and a MWD of 1.53.

Example 11

In this procedure, ethylene and propylene were copolymerized by adding, under a nitrogen atmosphere, 0.2 ml of a 25 wt. % solution of triethylaluminum in hexane followed by 10 ml of a toluene solution containing 36 mg of bis(cyclopentadienyl)hafnium dimethyl and 11 mg of N,N-dimethylanilinium tetrakis(pentafluorophenyl)boron to a 1 liter stainless-steel autoclave previously flushed with nitrogen. Propylene (400 ml) was then added to the autoclave which heated to 40° C. and further pressurized with 200 psig of ethylene. After 30 minutes, the autoclave was vented and opened. The yield of ethylene-propylene copolymer was 65 g. The copolymer contained 67 wt. % ethylene, and had a molecular weight of 210,000 and a molecular weight distribution of 1.98. Under similar conditions, but in the absence of triethylaluminum, 37 grams of an ethylene-propylene copolymer were obtained with an ethylene content of 56 wt. %, a molecular weight of 548,000 and a molecular weight distribution of 1.66.

Example 12

The procedure of Example 11 was repeated using 0.2 mmole triethylborane, instead of triethylaluminum, and a toluene solution (10 ml) containing 24 mg of bis(cyclopentadienyl)hafnium dimethyl and 8 mg of tetrakis(pentafluorophenyl)boron. The yield of ethylene-propylene copolymer was 10.8 g. The copolymer contained 60.8 wt. % ethylene, and had a $M_w$ of 508,000 and a MWD of 1.74. Under similar conditions, but in the absence of triethylborane, 2.0 g of polymer were obtained with an ethylene content of 31.9 wt. %, a $M_w$ of 541,000 and a MWD of 1.88.

The invention has been described with reference to its preferred embodiments. Those of skill in the art may appreciate from the description changes and modifications which may be made which do not depart from the scope and spirit of the invention as described above and claimed hereafter.

We claim:

1. A method of polymerizing ethylene, α-olefins, diolefin, cyclic olefins, acetylenically unsaturated monomers or mixtures of these monomers, comprising the steps of:
   (I) contacting such monomer or monomer mixture with a catalyst system comprising,
   (a) a reaction product of
   (i) a bis(cyclopentadienyl)Group IV-B metal compound; and
   (ii) an activator compound comprising
   (1) a cation which will irreversibly react with at least one ligand of the Group IV-B metal compound, and
   (2) a labile, bulky anion which is a single coordination complex having a plurality of lipophilic radicals or a plurality of boron atoms covalently coordinated to and shielding a central charge-bearing metal or metalloid atom;
   (b) an organometallic additive compound; and
   (II) continuing the contacting step of (I) for a sufficient period of time to polymerize at least a portion of the monomer.

2. The method of claim 1 wherein the additive compound is represented by the formula:

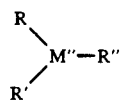

wherein M" is a Group III-A element; each of R,R' and R" is a straight or branched chain alkyl radical of $C_1-C_{20}$ in carbon number, and R" may be an alkoxide radical.

3. The method of claim 2 wherein the catalyst system comprises a ratio of activator to Group IV-B metal compound from about 1:1 to about 20:1.

4. The method of claim 3 the catalyst system comprises a molar ratio of Group III-A element compound to activator compound of from about 0.1:1 to about 200:1.

5. The method of claim 4 wherein the contacting of step (I) is maintained at a temperature of from about −100° to about 300° C.

6. The method of claim 5 wherein the bis(cyclopentadienyl) Group IV-B metal compound is represented by one of the following general formulae:

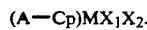  1

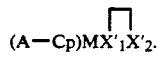  2

(A—Cp)ML.  3

  4 wherein
M is a Group IV-B metal;
(A—Cp) is either (Cp)(Cp*) or Cp—A'—Cp* and Cp and Cp* are the same or different substituted or unsubstituted cyclopentadienyl radical;
A' is a covalent bridging group;
L is an olefin, diolefin, or aryne ligand;

$X_1$ and $X_2$ are, independently, hydride radical, hydrocarbyl radical, substituted-hydrocarbyl radical, or organometalloid radical; or $X'_1$ and $X'_2$ are joined and bound to the M metal atom to form a metallacycle, in which the M metal atom, $X'_1$ and $X'_2$ form a hydrocarbocyclic ring containing from about 3 to about 20 carbon atoms; and p1 R is a substituent on one cyclopentadienyl radical which is bound to the M metal atom.

7. The method of claim 6, wherein said activator compound is represented by the following general formulae:

$$[(L'-H)^+]_d[(M')^{m+}Q_1Q_2\ldots Q_n]^{d-}$$

wherein:

L' is a neutral Lewis base, H is a hydrogen atom, and [L'—H] is a Bronsted acid;

M' is a metal or metalloid selected from Groups V-B, VI-B, VII-B, VIII, I-B, II-B, III-A, IV-A and V-A;

$Q_1$ to $Q_n$ are, independently, hydride radical, dialkylamido radical, alkoxide radical, aryloxide radical, hydrocarbyl radical, substituted-hydrocarbyl radical or organometalloid radical and any one, but not more than Q1 to Qn halide;

m is an integer from 1 to 7;

n is an integer from 2 to 8; and $n-m=d$.

8. The method of claim 2, wherein the Group III-A element compound comprises a trialkylaluminum, a trialkylborane or mixtures thereof.

9. The method of claim 7, wherein said activator compound is represented by the following general formula:

$$[L'-H]^+[BAr_1Ar_2X_3X_4]^-$$

wherein:

L' is a neutral Lewis base, H is a hydrogen atom, and [L'—H]$^+$ is a Bronsted acid;

B is boron in a valence state of 3;

$Ar_1$ and $Ar_2$ are the same or different aromatic or substituted-aromatic hydrocarbon radicals which radical may be linked to each other through a stable bridging group; and $X_3$ and $X_4$ are, hydride radical, halide radical, hydrocarbyl radical substituted-hydrocarbyl radical, or an organometalloid radical.

10. The method of claim 9, wherein said activator compound is a trisubstituted ammonium salt of a substituted aromatic boron compound.

11. The method of claim 10, wherein said activator compound is tri(n-butyl)ammonium tetrakis(pentafluorophenyl)boron or N,N-dimethylanilinium tetrakis(pentafluorophenyl)boron.

12. The method of claim 11, wherein the metallocene component is a chiral component.

13. The method of claim 12, wherein prochiral olefins are polymerized to stereoregular polymers.

14. The method according to claim 1, wherein the catalyst system is supported on silica, alumina or mixtures thereof.

15. The method according to claim 14, wherein the catalyst system is prepolymerized.

* * * * *